United States Patent
Sabbahi

(10) Patent No.: US 12,121,473 B2
(45) Date of Patent: Oct. 22, 2024

(54) AIR FLOW SYSTEM WITH A PROXIMAL CONNECTOR AND A FLOW CHAMBER

(71) Applicant: Wesam Sabbahi, Houston, TX (US)

(72) Inventor: Wesam Sabbahi, Houston, TX (US)

( * ) Notice: Subject to any disclaimer, the term of this patent is extended or adjusted under 35 U.S.C. 154(b) by 1019 days.

(21) Appl. No.: 17/092,321

(22) Filed: Nov. 8, 2020

(65) Prior Publication Data
US 2021/0052417 A1    Feb. 25, 2021

Related U.S. Application Data

(63) Continuation-in-part of application No. 15/764,850, filed on Mar. 29, 2018, now Pat. No. 10,828,190.

(51) Int. Cl.
*A61F 7/00* (2006.01)

(52) U.S. Cl.
CPC .......... *A61F 7/0085* (2013.01); *A61F 7/0053* (2013.01); *A61F 2007/0055* (2013.01)

(58) Field of Classification Search
CPC ........ A61F 7/0085; A61F 7/00; A61F 7/0053; A61F 7/0097; A61F 2007/0095; A61F 2007/0093; A61F 2007/0091; A61F 2007/0064; A61F 2007/0052; A61F 2007/006; A61F 2007/0072; A61F 2007/0096; A61F 2007/0086; A61F 2007/0055; A61F 2007/0057; A61F 2007/0062; A61F 2007/0054; A62B 7/12; A61M 61/08
See application file for complete search history.

(56) References Cited

U.S. PATENT DOCUMENTS

| | | | |
|---|---|---|---|
| 4,007,737 A | 2/1977 | Bernard | |
| 2013/0238042 A1 | 9/2013 | Gilldersleeve | |
| 2014/0102452 A1* | 4/2014 | Forrester | A61M 16/0875 128/204.18 |

FOREIGN PATENT DOCUMENTS

SU    1174028 A    8/1985

* cited by examiner

*Primary Examiner* — Joseph A Stoklosa
*Assistant Examiner* — Adam J Avigan
(74) *Attorney, Agent, or Firm* — Craft Chu PLLC; Andrew W. Chu

(57) ABSTRACT

The air flow system includes a hose member having an exterior flow channel and an interior flow channel, a distal connector, a proximal connector, and a flow chamber. The air flow in the interior flow channel is separate from the exterior flow channel. Air flows from the exterior flow channel, through a flow chamber, around a treatment site of inflammation and back to the interior flow channel. The system for air circulation therapy also includes a connector to the hose member, an air pump supply in an inner chamber, and an air recovery unit in an outer chamber. The proximal connector includes a nozzle head, a tubular sleeve, a first set of slot openings, a second set of slot openings, a cover sleeve, and a locking ring. The system includes the flow chamber of a flexible polymeric material.

20 Claims, 6 Drawing Sheets

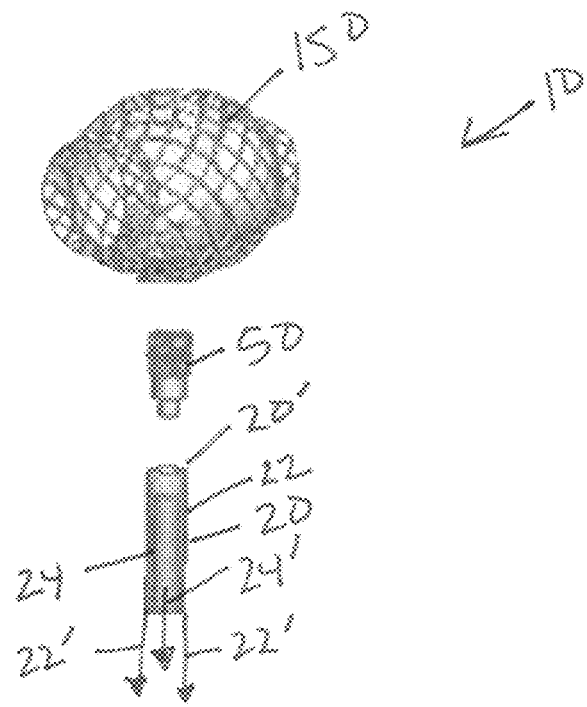
FIG. 1
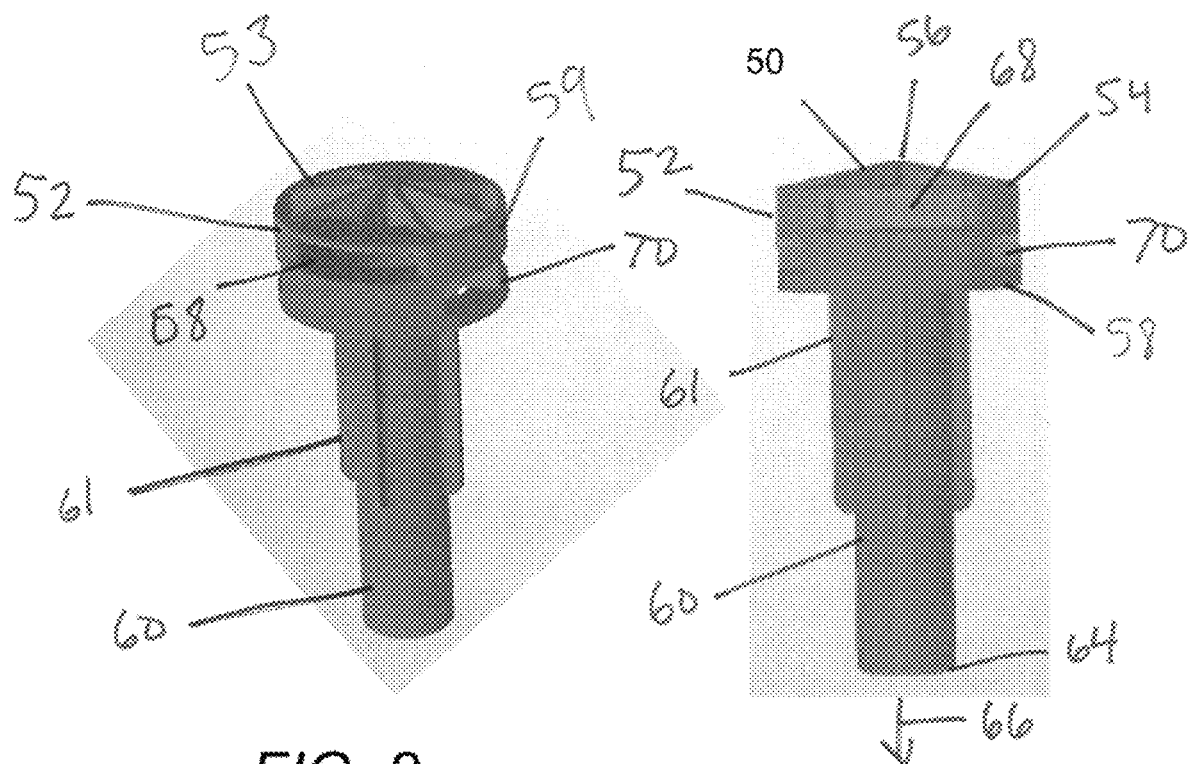
FIG. 2
FIG. 3

FIG. 12
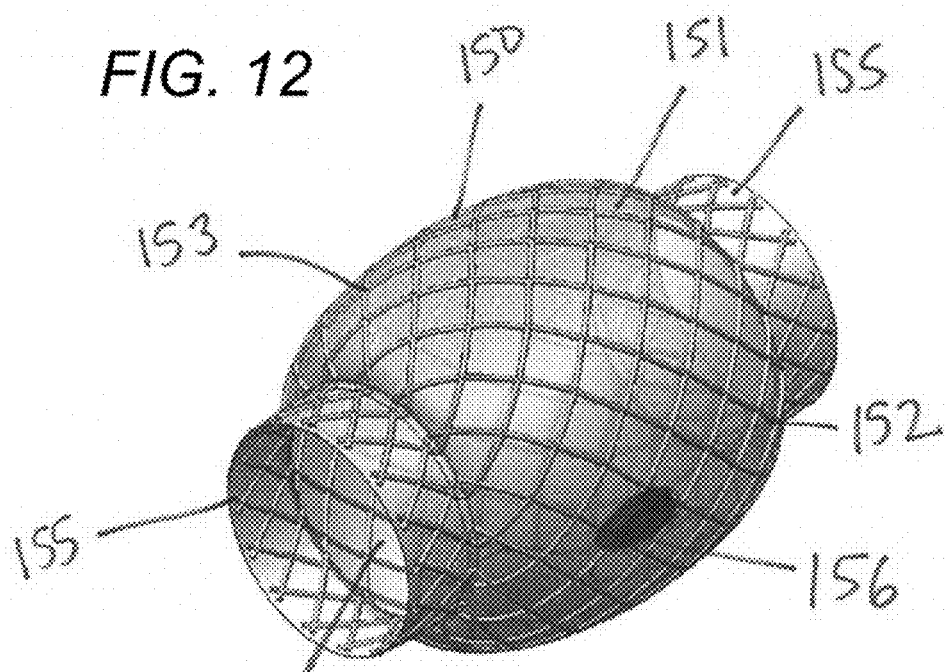
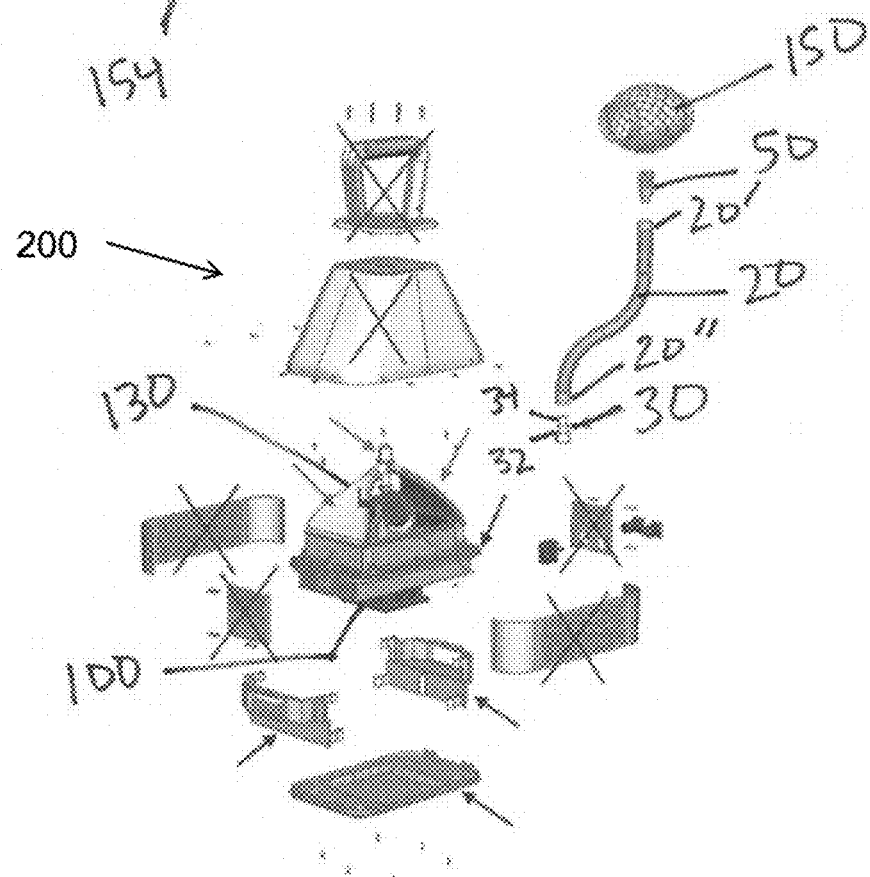
FIG. 13

AIR FLOW SYSTEM WITH A PROXIMAL CONNECTOR AND A FLOW CHAMBER

CROSS-REFERENCE TO RELATED APPLICATIONS

The present application claims priority under 35 U.S.C. Section 120 from U.S. patent application Ser. No. 15/764,850, filed on 29 Mar. 2018, entitled "AIR FLOW SYSTEM AND METHOD FOR AIR CIRCULATION THERAPY". See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to a system and method for air circulation therapy. The present invention relates to an air flow system supplying air with temperature, speed and direction control. The present invention relates to a system for air circulation or air convection therapy. More particularly, the present invention relates to an air flow with temperature controlled to treat inflammation and for rehabilitation of injury.

2. Description of Related Art Including Information Disclosed Under 37 CFR 1.97 and 37 CFR 1.98

Pain, heat, redness, swelling, and loss of function are the responses to inflammation in the body. Inflammation is a protective response to harmful stimuli, such as damaged cells from a soft tissue injury, a germ or even a virus, or irritants. Inflammation is part of the immune system, as a defense system of the body, involving immune cells, other molecules, and blood flow. In particular, white blood cells and chemicals of the immune system can fight infection and foreign substances, such as bacteria and viruses. Inflammation begins tissue repair and removes dead or damaged cells from the tissue.

Acute inflammation moves blood into the injured tissue, usually as an initial reaction to an injury. Plasma and white bloods cells may be the first to arrive, but eventually a full immune response is brought to the injured tissue. Chronic inflammation is a protracted exposure of the injured tissue to the new cells triggered by the immune response. New damage to the tissue is caused by the inflammation, while the inflammation repairs the tissue at the same time.

Treatments for inflammation are known. Medication can address the pain aspect. Conventional treatments also include RICE (Rest, Ice, Compression and Elevation). Rest reduces the strain on the injured tissue. Ice or cold therapy causes vasoconstriction, which limits blow flow to the injured tissue. Compression and Elevation also address swelling and pain of inflammation.

In the area of cold therapy, ice packs are basic treatments. A cloth covered ice pack can be applied to the injured tissue. However, there are limitations. Ice packs can only be effective at limited exposures. An ice pack can cause cold burns and frostbite, if placed on or directly against injured tissue for too long, especially for elderly individuals with thinner skin.

It is also known to use heat therapy to treat inflammation, usually for rehabilitation purposes. The increased blood flow releases joint stiffness, decreases pain, and brings oxygen to the injured, yet healing, tissues.

While cold therapy has traditionally been used for acute inflammation and initial treatment of an injury, and heat therapy has traditionally been used for rehabilitation purpose, there is a need for a system to provide both as temperature controlled therapy.

In the past, various patents and patent publications have disclosed systems for temperature control therapy include both cold therapy and heat therapy.

U.S. Pat. No. 8,105,370, issued to Augustine, Scott on 31 Jan. 2012, discloses an inflatable thermal blanket. The inflatable blanket delivers airflow to the body and therapy site. There is a surgical drape as a window through the blanket so that surgeons can reach through the blanket and into the patient for surgery. The blanket control temperature of the body and therapy site or surgical site by controlling hot or cold air through the blanket.

U.S. Patent Publication No. 20110098792, published for Lowe, Mark H. et al on 28 Apr. 2011, teaches a therapeutic wrap for temperature-controlled therapy. A fluid bladder having an inlet, an outlet, and at least one fluidic channel is incorporated into the therapeutic wrap. Controlling the temperature of the fluid flowing through the fluidic channel controls the delivery of hot or cold to the therapy site, when the wrap is worn on the body part with the therapy site. The therapy wrap may include insulating layers to further control the delivery of hot or cold to the therapy site.

U.S. Patent Publication No. 20150216718, published for Diller, Kenneth R., et al on 6 Aug. 2015, describes another device for thermoelectric heating and cooling of mammalian tissue. A plurality of thermoelectric modules with temporal and spatial dimensions is placed on the tissue. Each module can be controlled to deliver hot or cold to the surface of the tissue and the coordination of modules can deliver set patterns of hot and cold in programmed sequences and different durations.

In the prior art, it is also known to deliver hot and cold by fluid or air flow. Air flow is known to be temperature controlled so as to provide a heat source and cool source to a therapy site on the body.

U.S. Patent Publication No. 20130238042, published for Gildersleeve, Richard et al, on 12 Sep. 2013, discloses a system and method for providing temperature-controlled therapy. A therapeutic wrap delivers temperature-controlled air or other gas to the therapy site on the body of the patient. Intended for orthopedic or other injuries, the therapy site is exposed to different temperatures for a variable amount of time. There are also feedback mechanisms for patient control of the temperature of the gas.

U.S. Patent Publication No. 20090270910, published for Hargens, Alan R., et al on 29 Oct. 2009, describes a method and apparatus for increasing blood flow in a body part. An enclosure is fitted to house an affected area of a body part. The enclosure is releasably sealed on the body part around the affected area, so as to form a substantially airtight enclosure. Air is pumped through a port to inflate the enclosure around the body part without contacting the area to be treated. The compression provided by the air pressure increases blood flow to the affected area without physically contacting the affected area. The pump is an air and vacuum pump for higher or lower pressure on the affected area.

It is an object of the present invention to provide a system for air circulation or air circumvection therapy.

It is an object of the present invention to provide a system for air convection therapy.

It is an object of the present invention to provide a system for air flow therapy with temperature control.

It is another object of the present invention to provide a system with controlled air flow for circulation therapy.

It is another object of the present invention to provide a system for temperature controlled therapy based on air convection.

It is still another object of the present invention to provide a system with controlled air flow and temperature control for treating inflammation.

It is yet another object of the present invention to provide an air flow system to control supplying air at a first temperature and recovering air at a second temperature from a flow chamber.

It is an object of the present invention to provide a proximal connector for an air flow system to control supplying air at a first temperature to a flow chamber and recovering air at a second temperature from the flow chamber.

It is an object of the present invention to provide a flow chamber with a flexible surface wall to actuate between an expanded configuration and a collapsed configuration.

It is an object of the present invention to provide a system for air circulation therapy with a connector to split air flow between an inner chamber and an outer chamber for separate recovery of air from the flow chamber and supply of air to the flow chamber.

These and other objectives and advantages of the present invention will become apparent from a reading of the attached specification.

BRIEF SUMMARY OF THE INVENTION

Embodiments of the present invention include the air flow system for supplying air at first temperature and a first speed and recovering air at a second temperature and a second speed. The flow path traveled by the air supplied includes circulating around inflammation on a body part of a patient and returning to the air flow system. The air flow system includes a hose member having an exterior flow channel, and an inner flow channel, and a distal connector having an outer sleeve with an outer sleeve flow channel and an inner sleeve with an inner sleeve flow channel. The interior flow channel recovers air, while the exterior flow channel supplies or delivers air.

Embodiments of the air flow system also include a proximal connector attached to the hose member closest to the treatment site of the inflammation. The proximal connector comprises a nozzle head, a tubular sleeve, a first set of slot openings, a second set of slot openings, a cover sleeve, and a locking ring. The nozzle head and the tubular sleeve are connected to each other and can be made integral with each other. The interior nozzle flow channel passes through both the nozzle head and the tubular sleeve. There is a first set of slot openings on the cylindrical side walls, and each slot opening is in fluid connection with the interior nozzle flow channel. The second set of slot openings on the cylindrical side walls are in fluid connection with the bottom end of the nozzle head. The cover sleeve is in removable sliding engagement with the tubular sleeve so as to form an exterior nozzle flow channel. The interior nozzle flow channel is in fluid connection with the inner flow channel of the hose member. The exterior nozzle flow channel is in fluid connection with the exterior flow channel of the hose member. Direction of the flow path is also affected by embodiments of the proximal connector.

Embodiments of the air flow system also includes a flow chamber. The flow chamber is comprised of a surface wall defining an interior volume, and an opening. The flow chamber has an expanded configuration and a collapsed configuration. The flow chamber is in fluid connection with both the interior nozzle flow channel and the exterior nozzle flow channel. The flow chamber can include the surface wall being comprised of a polymeric layer and a flexible mesh layer. There is an elasticity to transition between the expanded configuration and the collapsed configuration.

Embodiments of the present invention include a system for air circulation therapy. The system for air circulation includes the air flow system in the context of therapeutic equipment for treating a patient. Air circulation or air circumvection therapy is heating and cooling of the therapy site or treatment site by air flow to reduce inflammation and joint stiffness. The system includes a connector, an outer chamber with an air pump supply, and an inner chamber with an air recovery unit to complete the flow path of air.

A body part with a treatment site is placed within the flow chamber. Once closed to the body part, the air pump supply initiates an air flow through the exterior flow channel and second set of slot openings and to a treatment site in the flow chamber. Some air is returned from the flow chamber through the first set of slot openings and the interior flow channel to the air recovery unit in the inner chamber. The air treats the inflammation with heat or cold from the supplied air at the first temperature at a particular flow speed.

BRIEF DESCRIPTION OF THE SEVERAL VIEWS OF THE DRAWINGS

FIG. 1 is an exploded perspective view of an embodiment of the air flow system, according to the invention.

FIG. 2 is an upper perspective view of an embodiment of a nozzle head of a proximal connector of the air flow system of FIG. 1.

FIG. 3 is a side elevation view of the nozzle head of FIG. 2.

FIG. 12 is an upper perspective view of an embodiment of a flow chamber of the air flow system of FIG. 1.

FIG. 13 is an exploded perspective view of an embodiment of the system for air circulation therapy.

DETAILED DESCRIPTION OF THE INVENTION

Figure 4:
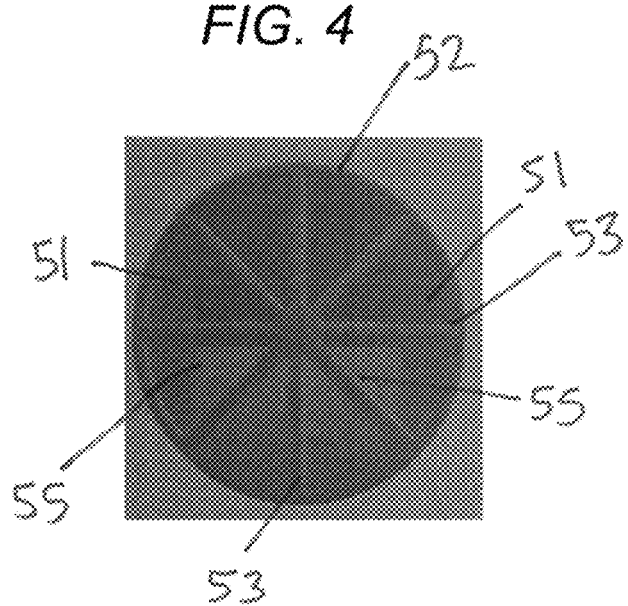
FIG. 4 is a top plan view of the nozzle head of FIG. 2.
Figure 5:
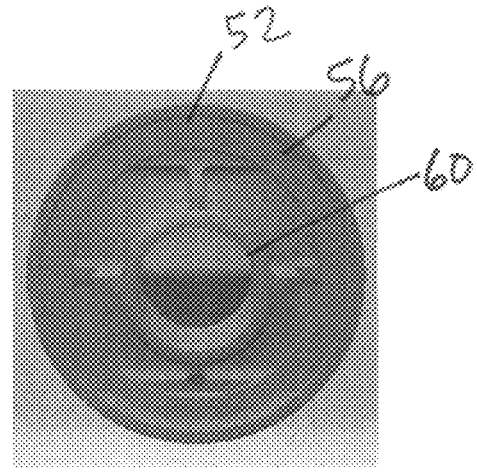
FIG. 5 is a bottom plan view of the nozzle head of FIG. 2.
Figure 6:
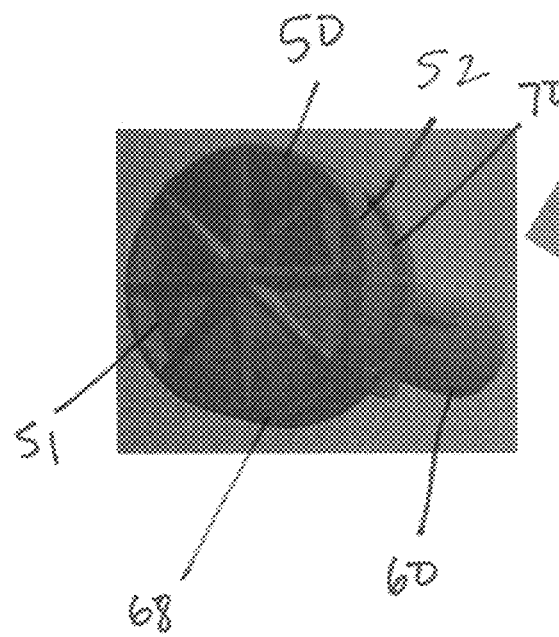
FIG. 6 is a side perspective view of the nozzle head of FIG. 2.
Figure 7:
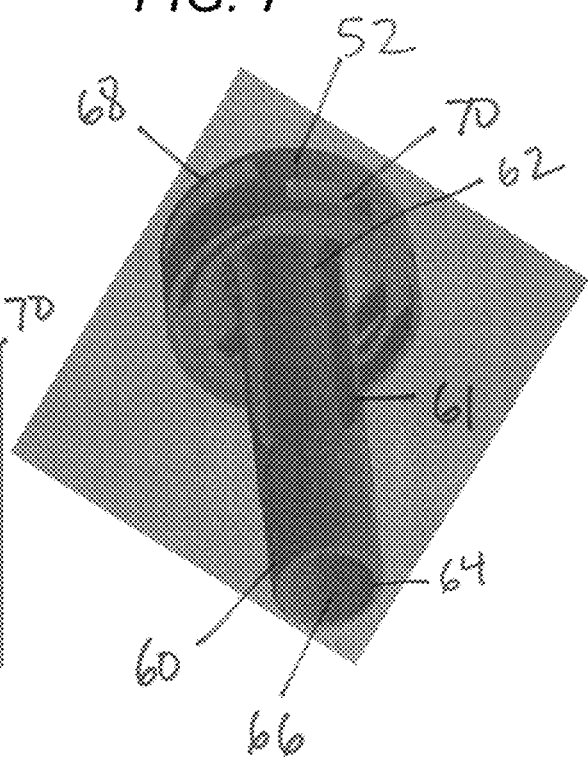
FIG. 7 is a back perspective view of the nozzle head of FIG. 2.

Referring to FIGS. 1-17, embodiments of the air flow system 10 of the present invention supplies air and recovers air. The temperature of the air supplied and the air recovered are different. The air supplied can be supplied at a first temperature. The flow path traveled by the air supplied includes circulating around inflammation on a body part of a patient and returning to the air flow system. The air recovered is at a second temperature and is vented away from the inflammation.

Embodiments of the air flow system 10 include a hose member 20 having a proximal end 20' and a distal end 20" opposite the proximal end. The hose member can have an exterior flow tube 22 forming an exterior flow channel 22', and an interior flow tube 24 forming an inner flow channel 24'. FIGS. 1 and 13-15 shows the hose member 20 without any particular surfacing. The interior flow tube 24 can be concentrically aligned with the exterior flow tube 22 so that both tubes 22, 24 are on the same axis. The interior flow tube 24 mounted within the exterior flow tube 22. The interior flow tube 24 and the exterior flow tube 22 may also be separate tubes. The interior flow channel 24' should be sealed with respect to the exterior flow channel 22' because the interior flow channel 24' recovers air, while the exterior flow channel 22' supplies or delivers air. The interior flow channel 24' may be within the exterior flow channel 22, but these flow channels 22', 24' are not in direct fluid communication within the hose member 20. The air supplied and the air recovered must be separate.

Figure 16:
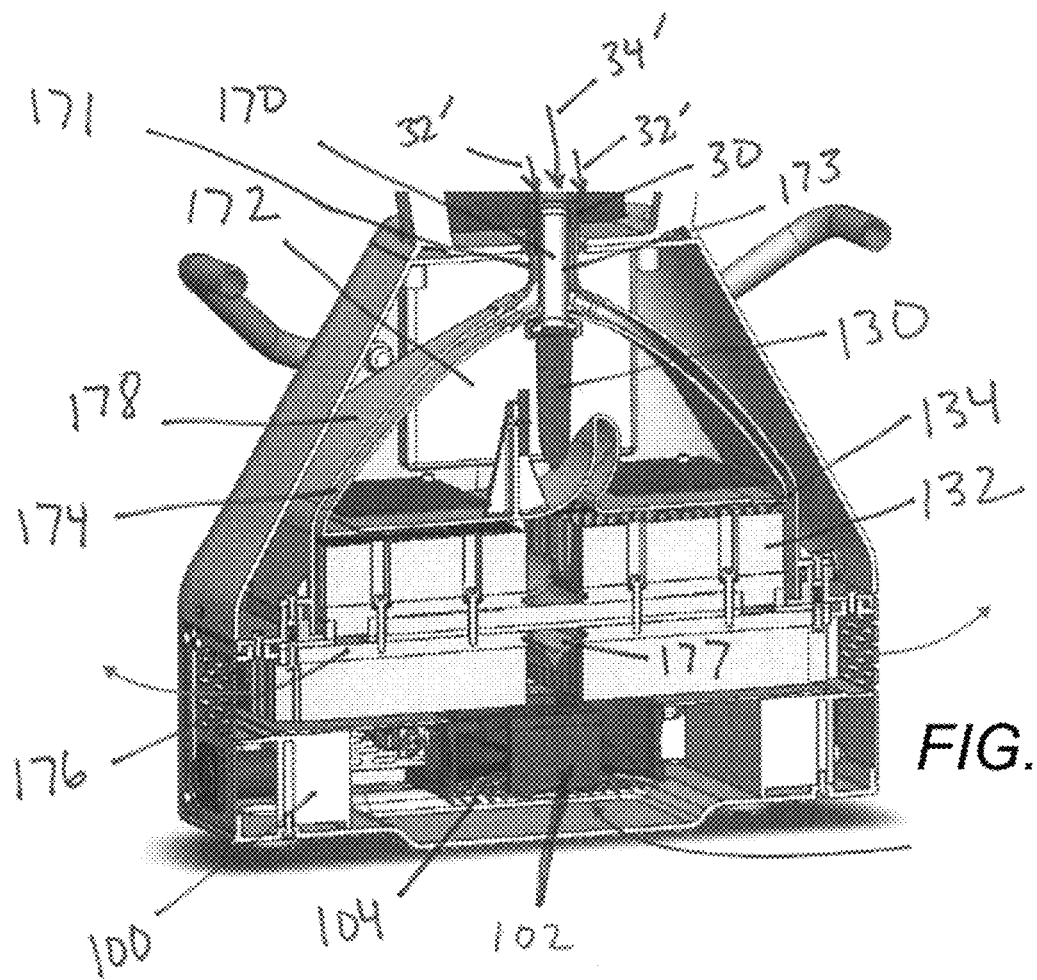
FIG. 16 is a partial sectional view of an embodiment of the air supply means and the air recovery unit means of the system of FIG. 13.
Figure 17:
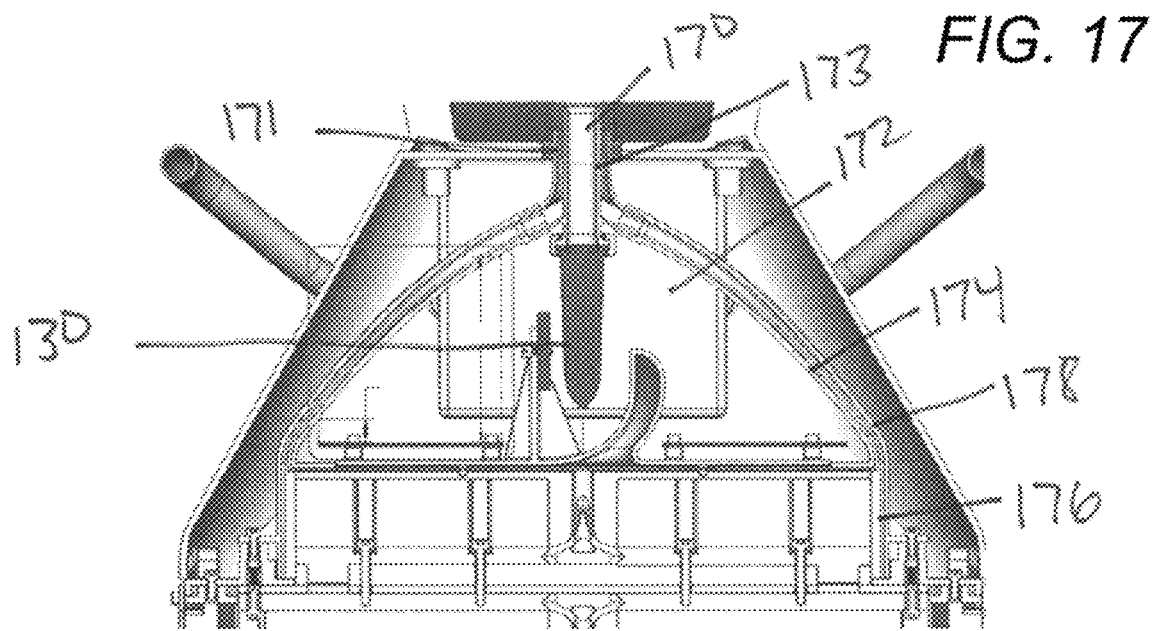
FIG. 17 is a partial sectional view of an embodiment of the air recovery unit means of the system of FIG. 13.

FIGS. 13 and 16 show embodiments of the distal connector 30 attached to the distal end 20" of the hose member 20. The distal connector 30 comprises an outer sleeve 32 having an outer sleeve flow channel 32', and an inner sleeve 34 having an inner sleeve flow channel 34'. The exterior flow channel 22' is in fluid connection with the outer sleeve flow channel 32', and the interior flow channel 24' is in fluid connection with the inner sleeve flow channel 34'.

FIGS. 1-11 show embodiments of a proximal connector 50 of the air flow system 10. The proximal connector 50 attaches to the proximal end 20' of the hose member 20. The proximal end 20' is closest to the treatment site of the inflammation. The proximal connector 50 is typically closer to the body part of the patient. The proximal connector 50 comprises a nozzle head 52, a tubular sleeve 60, a first set of slot openings 68, a second set of slot openings 70, a cover sleeve 72, and a locking ring 80. The nozzle head 52 has a top end 54 with a center point 56, a bottom end 58 opposite the top end, and cylindrical side walls 59 extending between the top end and the bottom end. The tubular sleeve 60 has a first sleeve end 62 attached to the nozzle head 52 and a second end 64 opposite the first sleeve end 62 so as to define an interior nozzle flow channel 66. The nozzle head 52 has a larger diameter than the tubular sleeve 60. The nozzle head 52 and the tubular sleeve 60 are connected to each other and can be made integral with each other. The interior nozzle flow channel 66 passes through both the nozzle head 52 and the tubular sleeve 60.

There is a first set of slot openings 68 on the cylindrical side walls 59, and each slot opening 68 is in fluid connection with the interior nozzle flow channel 66. The second set of slot openings 70 on the cylindrical side walls 59 are in fluid connection with the bottom end 58 of the nozzle head 52. The second set of slot openings 70 can be in an alternating arrangement with the first set of slot openings 68 around the nozzle head 52. The first set of slot openings 68 are closer to the top end 54, and the second slot openings 70 are closer to the bottom end 58.

Figure 10:
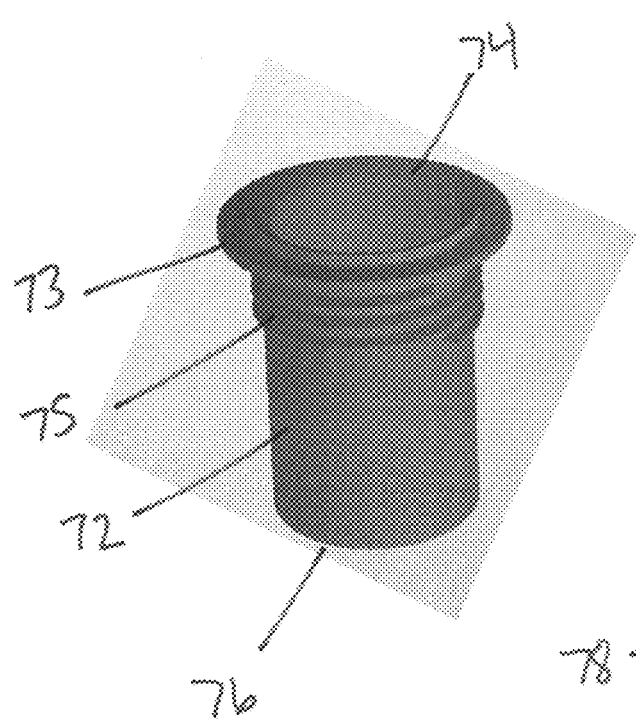
FIG. 10 is an upper perspective view of an embodiment of a tubular sleeve of the proximal connector of the air flow system of FIG. 1.
Figure 11:
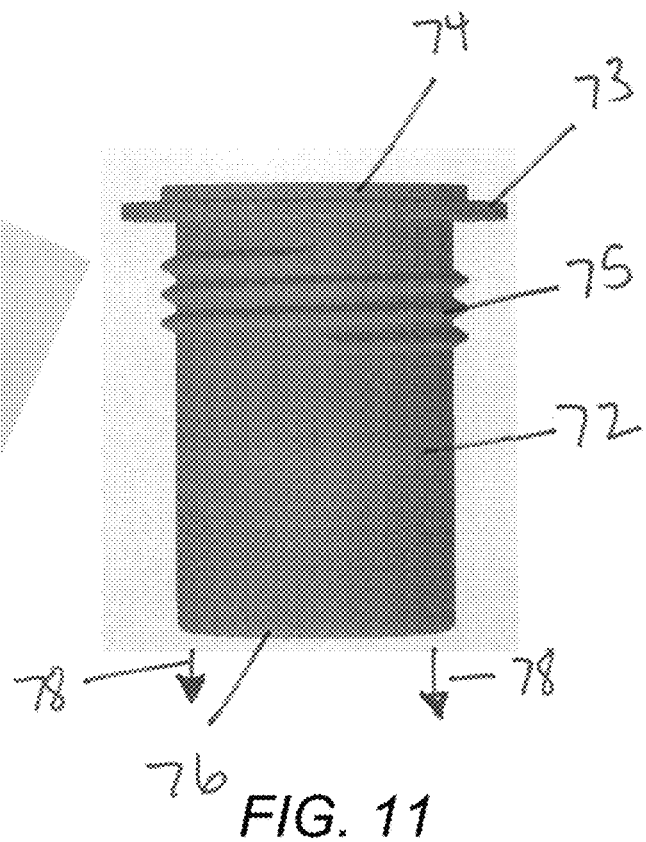
FIG. 11 is a side elevation view of the tubular sleeve of FIG. 10.
Figure 14:
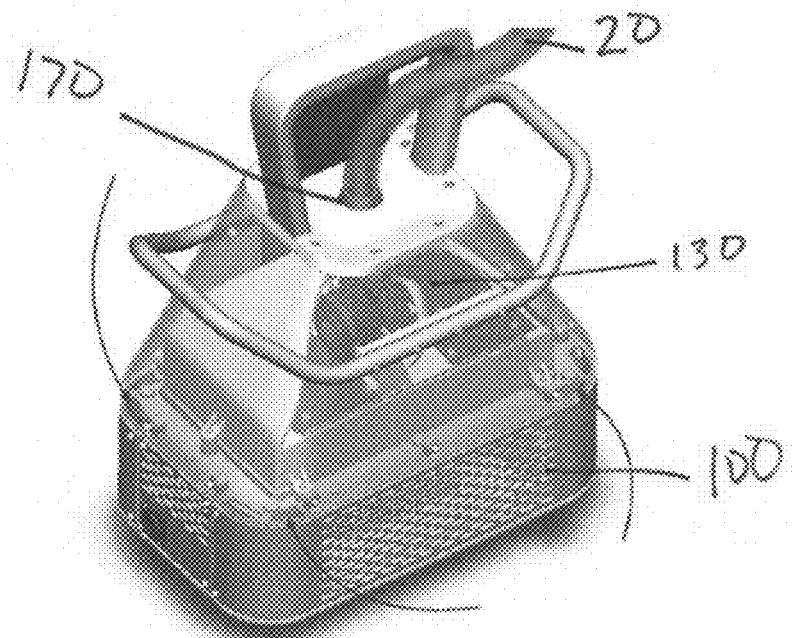
FIG. 14 is a partial perspective view of an embodiment of the air supply means and the air recovery unit means of the system of FIG. 13.
Figure 15:
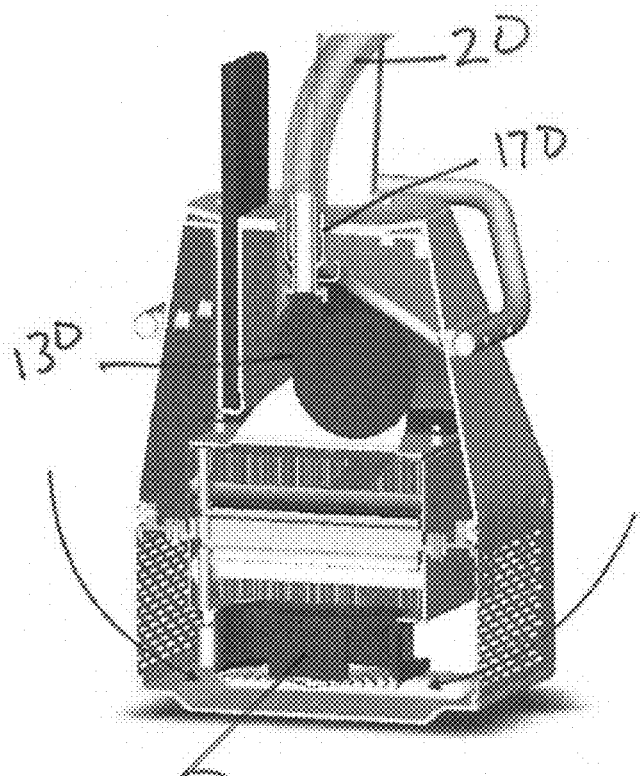
FIG. 15 is another partial perspective view of an embodiment of the air supply means and the air recovery unit means of the system of FIG. 13.

The cover sleeve 72 has a first cover sleeve end 74 and a second cover sleeve end 76 opposite the first cover sleeve end, according to FIGS. 10-11. The cover sleeve 72 is in removable sliding engagement with the tubular sleeve 60 so as to form an exterior nozzle flow channel 78 between the cover sleeve 72 and an exterior of the tubular sleeve 60. The interior nozzle flow channel 66 is in fluid connection with the inner flow channel 24' of the hose member 20. The exterior nozzle flow channel 78 is in fluid connection with the exterior flow channel 22' of the hose member 20. Thus, the exterior nozzle flow channel 78 is comprised of an interior of the cover sleeve 72 and an exterior of the tubular sleeve 60 in fluid connection with the second set of slot openings 70.

FIGS. 2, 3, 4 and 6 show the top end 54 being comprised of a plurality of top openings 51 in fluid connection with the second set of slot openings 70. The top end 54 can also be comprised of a plurality of baffles 53 radially arranged around the center 56. The embodiments show that the top end 54 can be further comprised of a plurality of slant portions 55 angled toward the top openings 51 so as to direct an air flow toward the top openings 51. FIGS. 2, 3, 4, and 6 show the slant portions 55 placed between adjacent baffles 53.

FIGS. 2, 3, 6, and 7 show the tubular sleeve 60 being comprised of a plurality of flanges 61 extending longitudinally along the tubular sleeve 60 from the first sleeve end 62 to the second sleeve end 64. Thus, the exterior nozzle flow channel 78 is further comprised of the interior of the cover sleeve 72, the exterior of the tubular sleeve 60, and the flanges 61. The flanges 61 can be distributed radially around the exterior of the tubular sleeve 60. The cover sleeve 72 is in removable sliding engagement over the tubular sleeve 60 as guided by the flanges 61.

Figure 8:
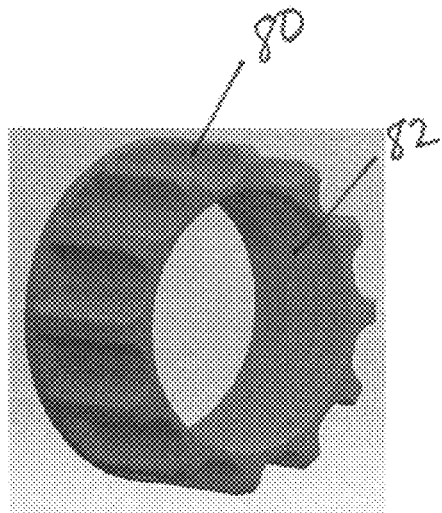
FIG. 8 is a side perspective view of an embodiment of a locking ring of the proximal connector of the air flow system of FIG. 1.
Figure 9:
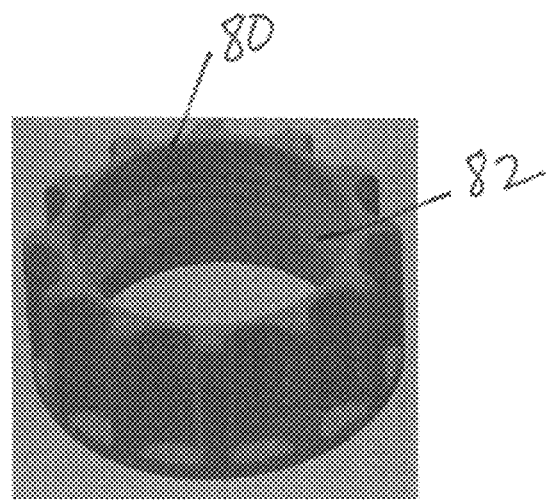
FIG. 9 is another perspective view of the locking ring of FIG. 8.

FIGS. 10-11 show the cover sleeve 72 being comprised of a rim portion 73 at the first cover sleeve end 74 and a sleeve threaded portion 75 between the rim portion 73 and the second cover sleeve end 76. The locking ring 80 of FIGS. 8-9 is in removable threaded engagement with the cover sleeve 72. The locking ring 80 can have a ring threaded portion 82 cooperative with the sleeve threaded portion 75 for removable threaded engagement of the locking ring 80 and the cover sleeve 72. The locking ring 80 seals the exterior nozzle flow channel 78. The second set of slot openings 70 are in fluid connection through the bottom end 58 of the nozzle head 52. From the bottom end 58 of the nozzle head 52, the rim portion 73 directs air flow to the interior of the cover sleeve 72 and an exterior of the tubular sleeve 60. The locking ring 80 seals that junction between the bottom end 58 and the rim portion 73. Air flow from the exterior flow channel 22' of the hose member 20 passes through the exterior nozzle flow channel 78 and through the second set of slot openings 70.

Embodiments of the air flow system 10 include an air pump supply means 100 being removably connected to the exterior nozzle flow channel 78 through the exterior flow channel 22' of the hose member 20, and an air recovery unit means 130 being removably connected to the interior nozzle flow channel 66 through the inner flow channel 24' of the hose member 20. The air pump supply means 100 provides air flow at a controlled temperature through the second set of slot openings 70. The air pump supply means 100 provides air flow through the exterior nozzle flow channel 78. The air recovery unit means 130 collects air from the flow chamber 150 through the first set of slot openings 68. The air collected is at a different temperature than the controlled temperature of the air flow at the second set of slot openings 70.

The air flow system 10 can also include a flow chamber 150 as in FIG. 1. FIG. 12 shows an embodiment of a flow chamber 150 being comprised of a surface wall 152 defining an interior volume 154, and an opening 156. The flow chamber 150 has an expanded configuration and a collapsed configuration. The flow chamber 150 is in fluid connection with both the interior nozzle flow channel 66 and the exterior nozzle flow channel 78. The proximal connector 50 is removably attached to the opening 156 for sealed engagement between the interior nozzle flow channel 66 and the flow chamber 150 and between the exterior nozzle flow channel 78 and the flow chamber 150.

When the proximal connector 50 includes the cover sleeve 72 being comprised of a rim portion 73 at the first cover sleeve end 72 and a sleeve threaded portion 75 between the rim portion 73 and the second cover sleeve end 74, and when the locking ring 80 has a ring threaded portion 82 cooperative with the sleeve threaded portion 75, as shown in FIGS. 8-11, the locking ring 80 is in removable threaded engagement with the cover sleeve 72. The opening 156 of the flow chamber 150 can be in sealed engagement between the rim portion 73 and the locking ring 80. The rim portion 73 and the locking ring 80 clamp the surface wall 152 around the opening 156 for the sealing engagement.

Other embodiments of the flow chamber 150 in FIG. 12 include the surface wall 152 being comprised of a polymeric layer 151 and a flexible mesh layer 153. The polymeric layer 152 can be comprised of polyurethane. The flexible mesh layer 153 is exterior to the polymeric layer 151. The flexible mesh layer 153 has a different elasticity than the polymeric layer. The polymeric layer 151 is used to seal the flow chamber 150 so that air does not escape. The flexible mesh layer 153 is restrictive and contracts to seal against the limb of a patient. The two different layers allow for the different adjustments for the sealing capability to the limb of the patient and volume capability of the flow chamber. There is an elasticity to transition between the expanded configuration and the collapsed configuration. Additional embodiments of the flow chamber 150 include a plurality of cuff portions 155 at opposite ends of the flow chamber 150 so as to seal the interior volume 154 of the flow chamber 150. The cuff portions 155 seal and grip to the limb of a patient so that the expanded configuration forms the interior volume 154 around the treatment site of the patient. The expanded configuration is an inflated setting with the surface wall 152 not in contact with the body part or therapy site. The flow chamber 150 also has a collapsed configuration with less air flow through the interior volume 154 than the expanded configuration. The deflated setting with the collapsed configuration has less air flow or no air flow so that the flow chamber 150 can be removed from the body part. There may be contact against the body part by the surface wall 152 in the collapsed configuration.

The present invention also includes the system 200 for air circulation therapy as shown in FIGS. 13-17. The system 200 for air circulation includes the air flow system 10 and the flow chamber 150 in the context of therapeutic equipment for treating a patient. Air circulation or air circumvection therapy is heating and cooling of the therapy site or treatment site by air flow to reduce inflammation and joint stiffness. Other uses of a temperature regulated environment are also possible. The temperature controlled therapy of the prior art, such as ice packs and heating pads, require surface contact with the injured tissue. Treatment of open wounds or injuries within a joint was not possible or ineffective. Other air flow therapies relied on compression from air pressure to treat inflammation or only use air temperature for treatment. In the present invention, moving air with convection effects more efficiently treat the injury. The temperature controlled moving air of different speeds of the present invention penetrates heating or cooling into injured tissue deeper than surface treatments. The system 200 delivers heated or cooled air at various speeds to address inflammation or other health conditions.

Embodiments of the system 200 includes a connector 170 being removably attached to the hose member 20, an inner chamber 172, and an outer chamber 176. The inner chamber 172 has an inner shell 174 and is in fluid connection with the connector 170. The outer chamber 176 has an outer shell 178 and is in fluid connection with the connector 170. The interior nozzle flow channel 66 is in fluid connection with the inner flow channel 24' of the hose member 20 and the inner chamber 172. The exterior nozzle flow channel 78 is in fluid connection with the exterior flow channel 22' of the hose member 20 and the outer chamber 176. The connector 170 can be comprised of an outer duct 171 and an inner duct 173 within the outer duct 171. The inner duct 173 is in fluid connection with the inner chamber 172. The outer duct 171 is in fluid connection with the outer chamber 176 around the inner chamber 172.

In FIGS. 13-17 of the system 200, the air pump supply means 100 is comprised of a fan means 102 and a temperature regulation means 104. The fan means 102 of the air pump supply means 100 can include a pump, a fan, blower or other device. There can also be an accelerator for additionally regulating the speed of air. The temperature regulation means 104 can include a heat exchanger, radiator, a compressor or other device. Any known heat exchanger can be used, such as one with the air passing over a coiled tube of a set temperature. Thus, the air pump supply means 100 generates air flow of a certain temperature with the temperature regulation means 104. Heated air and cooled air can be generated at a particular speed. Similarly, the air recovery unit means 130 can be comprised of a respective fan means 132 and a respective temperature regulation means 134. The respective fan means 132 may also be a pump, fan, blower or other device, and the respective temperature regulation means 134 may also be a heater, heat exchanger, compressor, or other device. The air recovery unit means 130 receives the vented exhaust from the treatment site, so that air may be hotter or cooler than the air delivered by the air pump supply means 100.

In the present invention of FIGS. 13-17, the air recovery unit means 130 and the inner shell 174 are above the air pump supply means 100. The inner shell 174 is housed within the outer shell 178. The outer chamber 176 can have a flow baffle 177 to guide air flow around the inner shell to the connector 170.

The method for treating inflammation uses the air flow system 10 as assembled. The proximal connector 50 is attached to a flow chamber 150 so that the exterior flow tube channel 22' and the interior flow tube channel 24' are in fluid connection with the interior volume 154. A body part with the treatment site 202 is inserted within the flow chamber 150, and then, the flow chamber is closed or sealed to the body part with the treatment site within the interior volume 154. An air pump supply means 100 is connected to the exterior flow tube channel 22', and an air recovery unit means 130 is connected to the interior flow tube channel 24'. Air flows from the air pump supply means 100 to the flow chamber 150 at a first temperature through the exterior flow tube 22 so as to fill the flow chamber 150. The air treats the inflammation with heat or cold at a particular flow speed. Then, air is vented from the flow chamber at a second temperature through the interior flow tube 24 to the air recovery unit means 130. When a temperature sensor and an air flow sensor are mounted in fluid connection with the flow chamber 150, the collected feedback data from the temperature sensor and the air flow sensor confirm the first temperature and the second temperature and other parameters. The air pump supply means and the air recovery unit means can be adjusted according to the feedback data by a control means connected to the air pump supply means, the air recovery unit means, the temperature sensor and the air flow sensor. Besides temperature, flow rate of the air pump supply means and air recovery unit means may also be used to make adjustments to the air pump supply means and air recovery unit means.

The present invention provides a system and method for a flow chamber with air flow of a particular temperature and speed. Treatment of inflammation and therapeutic uses for joints are examples of practical uses of the system, but other applications are possible. Air circulation or air circumvection of the system uses heating and cooling from moving air to reduce inflammation at the therapy or treatment site. Movement of air, not just temperature and pressure of air, can be used in other fields. Air convection with controlled temperature and speed of air flow along the flow path of the present invention provides moving heated or cooled air to a therapy site on the body part. The temperature controlled therapy is based on moving air, not just heated air. The convection currents more thoroughly and deeply penetrate into injured tissue without the risk of cold burns and other surface contact risks to the body part. The system provides controlled air flow and temperature control for treating inflammation.

Embodiments of the present invention supply air at a first temperature and first speed and recover air at a second temperature and a second speed from a flow chamber. The inflammation or other treatment site in the flow chamber receives the heat or cold and air movement for treatment. With the flow chamber closed, some of the air can be recovered or at least recycled back into the system. The flow path of air in the system includes air supplied to the flow chamber and air recovered from the flow chamber. Before the recovery, the treatment site, such as inflammation, on a patient's body is exposed to air flow at a regulated temperature, speed, and direction. The air flow speed and air temperature together can be changed together or separate for desired therapeutic effects.

The present invention provides a proximal connector for an air flow system to control supplying air at a first temperature to a flow chamber and recovering air at a second temperature from the flow chamber. The present invention also provides a flow chamber with a flexible surface wall to actuate between an expanded configuration and a collapsed configuration. There is also a system for air circulation therapy with a connector to split air flow between an inner chamber and an outer chamber for separate recovery of air from the flow chamber and supply of air to the flow chamber.

The foregoing disclosure and description of the invention is illustrative and explanatory thereof. Various changes in the details of the illustrated structures, construction and method can be made without departing from the true spirit of the invention.

I claim:

1. An air flow system, comprising:
    a hose member having a proximal end and a distal end opposite said proximal end, said hose member being comprised of an exterior flow tube forming an exterior flow channel, and an interior flow tube forming an inner flow channel, said interior flow tube being concentrically aligned with and mounted within said exterior flow tube, said inner flow channel being sealed with respect to said exterior flow channel;
    a distal connector attached to said distal end of said hose member, wherein said distal connector comprises an outer sleeve having an outer sleeve flow channel, and an inner sleeve having an inner sleeve flow channel; and
    a proximal connector attached to said proximal end of said hose member,
    wherein said proximal connector comprises:
    a nozzle head having a top end with a center point, a bottom end opposite said top end, and cylindrical side walls extending between said top end and said bottom end;
    a tubular sleeve having a first sleeve end attached to said nozzle head and a second end opposite said first sleeve end so as to define an interior nozzle flow channel:
    a first set of slot openings on said cylindrical side walls being in fluid connection with said interior nozzle flow channel:
    a second set of slot openings on said cylindrical side walls being in fluid connection with said bottom end:
    a cover sleeve having a first cover sleeve end and a second cover sleeve end opposite said first cover sleeve end, said cover sleeve being in removable sliding engagement with said tubular sleeve so as to form an exterior nozzle flow channel between said cover sleeve and an exterior of said tubular sleeve; and
    a locking ring in removable threaded engagement with said cover sleeve,
    wherein said interior nozzle flow channel is in fluid connection with said inner flow channel of said hose member, and
    wherein said exterior nozzle flow channel is in fluid connection with said exterior flow channel of said hose member.

2. The air flow system, according to claim 1, wherein said second set of slot openings are in an alternating arrangement with said first set of slot openings around said nozzle head, said first set of slot openings being closer to said top end, said second slot openings being closer to said bottom end.

3. The air flow system, according to claim 1, wherein said exterior nozzle flow channel is comprised of an interior of said cover sleeve and an exterior of said tubular sleeve in fluid connection with said second set of slot openings.

4. The air flow system, according to claim 1, wherein said top end is comprised of a plurality of top openings in fluid connection with said second set of slot openings.

5. The air flow system, according to claim 4, wherein said top end is comprised of a plurality of baffles radially arranged around said center.

6. The air flow system, according to claim 5, wherein said top end is comprised of a plurality of slant portions angled toward said top openings so as to direct an air flow toward said top openings.

7. The air flow system, according to claim 6, wherein said slant portions are placed between adjacent baffles.

8. The air flow system, according to claim 1, wherein said tubular sleeve is comprised of a plurality of flanges extending longitudinally along said tubular sleeve from said first sleeve end to said second sleeve end, and wherein said exterior nozzle flow channel is further comprised of said flanges.

9. The air flow system, according to claim 8, wherein said flanges are distributed radially around said exterior of said tubular sleeve.

10. The air flow system, according to claim 1, wherein said cover sleeve is comprised of a rim portion at said first cover sleeve end and a sleeve threaded portion between said rim portion and said second cover sleeve end, said locking ring having a ring threaded portion cooperative with said sleeve threaded portion for removable threaded engagement of said locking ring and said cover sleeve.

11. The air flow system, according to claim 1, further comprising:
an air pump supply means being removably connected to said exterior nozzle flow channel through said exterior flow channel of said hose member; and
an air recovery unit means being removably connected to said interior nozzle flow channel through said inner flow channel of said hose member.

12. A system for air circulation therapy, comprising:
a hose member having a proximal end and a distal end opposite said proximal end, said hose member being comprised of an exterior flow tube forming an exterior flow channel, and an interior flow tube forming an inner flow channel, said interior flow tube being concentrically aligned with and mounted within said exterior flow tube, said inner flow channel being sealed with respect to said exterior flow channel;
a distal connector attached to said distal end of said hose member, wherein said distal connector comprises an outer sleeve having an outer sleeve flow channel, and an inner sleeve having an inner sleeve flow channel;
a proximal connector attached to said proximal end of said hose member,
wherein said proximal connector comprises:
nozzle head having a top end with a center point, a bottom end opposite said top end, and cylindrical side walls extending between said top end and said bottom end;
a tubular sleeve having a first sleeve end attached to said nozzle end and a second end opposite said first sleeve end so as to define an interior nozzle flow channel:
a first set of slot openings on said cylindrical side walls being in fluid connection with said interior nozzle flow channel:
a second set of slot openings on said cylindrical side walls being in fluid connection with said bottom end:
a cover sleeve having a first cover sleeve end and a second cover sleeve end opposite said first cover sleeve end, said cover sleeve being in removable sliding engagement with said tubular sleeve so as to form an exterior nozzle flow channel between said cover sleeve and an exterior of said tubular sleeve; and
a locking ring in removable threaded engagement with said cover sleeve,
wherein said interior nozzle flow channel is in fluid connection with said inner flow channel of said hose member, and
wherein said exterior nozzle flow channel is in fluid connection with said exterior flow channel of said hose member;
a flow chamber being comprised of a surface wall defining an interior volume, and an opening, said flow chamber having an expanded configuration and a collapsed configuration, said flow chamber being in fluid connection with said interior nozzle flow channel and said exterior nozzle flow channel,
wherein said proximal connector is removably attached to said opening for sealed engagement between said interior nozzle flow channel and said flow chamber and between said exterior nozzle flow channel and said flow chamber;
a connector being removably attached to said hose member;
an inner chamber having an inner shell and being in fluid connection with said connector, an outer chamber having an outer shell and being in fluid connection with said connector, wherein said interior nozzle flow channel is in fluid connection with said inner flow channel of said hose member and said inner chamber, said exterior nozzle flow channel being in fluid connection with said exterior flow channel of said hose member and said outer chamber;
an air pump supply means being removeably connected to said exterior nozzle flow channel through said exterior flow channel of said hose member, said air pump supply means being housed within said outer chamber; and
an air recovery unit means being removeably connected to said interior nozzle flow channel through said inner flow channel of said hose member, said air recovery unit means being housed within said outer chamber.

13. The system, according to claim 12, wherein said cover sleeve is comprised of a rim portion at said first cover sleeve end and a sleeve threaded portion between said rim portion and said second cover sleeve end, said locking ring having a ring threaded portion cooperative with said sleeve threaded portion for removable threaded engagement of said locking ring and said cover sleeve, and
wherein said opening of said flow chamber is in sealed engagement between said rim portion and said locking ring.

14. The system, according to claim 12, wherein said surface wall is comprised of a polymeric layer and a flexible mesh layer.

15. The system, according to claim 14, wherein said polymeric layer is comprised of polyurethane.

16. The system, according to claim 14, wherein said flow chamber is further comprised of a plurality of cuff portions at opposite ends of said flow chamber so as to seal said interior volume of said flow chamber.

17. The system, according to claim 12, wherein said connector is comprised of an outer duct and an inner duct within said outer duct, said inner duct being in fluid connection with said inner chamber, said outer duct being in fluid connection with said outer chamber around said inner chamber.

18. The system, according to claim 12, wherein said air pump supply means is comprised of a fan means and a temperature regulation means, and wherein said air recovery unit means is comprised of another fan means and another temperature regulation means.

19. The system, according to claim 12, wherein said air recovery unit means and said inner shell are above said air pump supply means.

20. The system, according to claim 12, wherein said inner shell is housed within said outer shell.

* * * * *